(12) United States Patent
Colling et al.

(10) Patent No.: US 7,070,694 B2
(45) Date of Patent: Jul. 4, 2006

(54) PURIFICATION OF FLUID COMPOUNDS UTILIZING A DISTILLATION - MEMBRANE SEPARATION PROCESS

(75) Inventors: Craig W. Colling, Warrenville, IL (US); George A. Huff, Jr., Naperville, IL (US); Stephen J. Pietsch, Naperville, IL (US)

(73) Assignee: BP Corporation North America Inc., Warrenville, IL (US)

( * ) Notice: Subject to any disclaimer, the term of this patent is extended or adjusted under 35 U.S.C. 154(b) by 276 days.

(21) Appl. No.: 10/393,054

(22) Filed: Mar. 20, 2003

(65) Prior Publication Data
US 2004/0182786 A1    Sep. 23, 2004

(51) Int. Cl.
*B01D 15/00* (2006.01)

(52) U.S. Cl. .................... 210/640; 210/181; 210/175; 95/45; 95/50; 585/118; 203/19; 203/68; 203/71; 203/98

(58) Field of Classification Search ............... 210/640, 210/181, 175; 95/45, 50; 96/4; 585/118; 203/18, 68, 71, 98
See application file for complete search history.

(56) References Cited

U.S. PATENT DOCUMENTS

| 4,374,657 | A | * | 2/1983 | Schendel et al. ............ 62/624 |
| 4,444,571 | A | * | 4/1984 | Matson ........................ 95/48 |
| 4,857,078 | A | * | 8/1989 | Watler ......................... 95/50 |
| 4,952,751 | A | * | 8/1990 | Blume et al. ............... 585/818 |
| 4,978,430 | A | * | 12/1990 | Nakagawa et al. .......... 203/14 |
| 5,057,641 | A | * | 10/1991 | Valus et al. ................ 585/818 |
| 5,273,572 | A | * | 12/1993 | Baker et al. .................. 95/48 |
| 5,326,385 | A | * | 7/1994 | Rajani et al. ................. 95/46 |
| 6,187,987 | B1 | * | 2/2001 | Chin et al. ................. 585/819 |

* cited by examiner

*Primary Examiner*—Ana Fortuna
(74) *Attorney, Agent, or Firm*—Ekkehard Schoettle

(57) ABSTRACT

Apparatus and processes are disclosed for economical separation of fluid mixtures. Broadly, apparatus of the invention is an integrated fractional distillation and perm-selective membrane separation apparatus. More particularly, the integrated apparatus comprises a fractional distillation column and one or more membrane device utilizing solid perm-selective membranes. Processes of the invention are particularly useful for simultaneous recovery of a very pure permeate product, a desired non-permeate stream, and one or more distillate products from a fluid mixture containing at least two compounds of different boiling point temperatures.

7 Claims, 3 Drawing Sheets

PURIFICATION OF FLUID COMPOUNDS UTILIZING A DISTILLATION - MEMBRANE SEPARATION PROCESS

TECHNICAL FIELD

The present invention relates to processes for recovery of purified products from a fluid mixture by means of an integrated fractional distillation and perm-selective membrane separation apparatus. More particularly, the integrated apparatus of the invention comprises a fractional distillation column and one or more devices using solid perm-selective membranes for recovery of purified products. Apparatus of the invention is particularly useful for simultaneous recovery of a very pure permeate product, one or more products of distillation, and/or a desired non-permeate stream, from a fluid mixture containing at least two compounds of different boiling point temperatures.

BACKGROUND OF THE INVENTION

Membranes useful for the separation of gaseous mixtures are of two very different types: one is microporous while the other is nonporous. Discovery of the basic laws governing the selectivity for gases effusing through a microporous membrane is credited to T. Graham. When the pore size of a microporous membrane is small compared to the mean-free-path of non-condensable gas molecules in the mixture, the permeate is enriched in the gas of the lower molecular weight. Practical and theoretical enrichments achievable by this technique are very small because the molecular weight ratios of most gases are not very large and the concomitant selectivities are proportional to the square roots of these ratios. Therefore, a large number of separation stages is needed to effect an efficient separation of a given gas from a gaseous mixture. However, because this method of separation relies solely on mass ratios and not chemical differences among the effusing species, it is the only membrane based method capable of separating isotopes of a given element. For this reason, this method was chosen to enrich uranium in the fissionable isotope 235 for development of the atomic bomb during World War II. However, this method of separation is inherently expensive due to the large amount of capital investment needed for processing a necessary large amount of gas, stringent membrane specifications requiring high porosity and small pore size, and high energy requirements for operation.

In nonporous membrane systems, molecules permeate through the membrane. During permeation across the nonporous membrane, different molecules are separated due to the differences of their diffusivity and solubility within the membrane matrix. Not only does molecular size influence the transport rate of each species through the matrix but also the chemical nature of both the permeating molecules and the polymer matrix itself. Thus, conceptually useful separations should be attainable.

The art is replete with processes said to fabricate membranes possessing both high selectivity and high fluxes. Without sufficiently high fluxes the required membrane areas required would be so large as to make the technique uneconomical. It is now well known that numerous polymers are much more permeable to polar gases (examples include $H_2O$, $CO_2$, $H_2S$, and $SO_2$) than to nonpolar gases ($N_2$, $O_2$, and $CH_4$), and that gases of small molecular size ($He$, $H_2$) permeate more readily through polymers than large molecules ($CH_4$, $C_2H_4$).

Utilization of membrane separation has taken an important place in chemical technology for use in a broad range application. Gas separation has become a major industrial application of membrane technology in the last 15 years. Membrane based technology for the production of nitrogen from air, removal of carbon dioxide from natural gas, and purification of hydrogen now occupy significant shares of the markets for these processes.

Some of the most difficult separations in the petrochemical industry involve the separation of light olefins and paraffins. Due to their similar relative volatilities, energy-intensive, multi-trayed distillation columns are used for the purification of light olefins. The use membranes has been of interest for many years for the separation of olefins and paraffins. U.S. Pat. Nos. 3,758,603 and 3,864,418 in the names of Robert D. Hughes and Edward F. Steigelmann describe membranes used in conjunction with metal complexing techniques to facilitate the separation of ethylene from ethane and methane. Similar metal complex and membrane hybrid processes, called facilitated transport membranes, have been described in U.S. Pat. No. 4,060,566 in the name of Robert L. Yahnke and in U.S. Pat. No. 4,614,524 in the name of Menahem A. Kraus. Most of this work focused on details of the internals of the facilitated transport membrane device and not on how to incorporate them into a process that produced products that met market specifications.

Processes for the purification of olefins with membranes has focused on the use of facilitated transport membranes in conjunction with distillation columns. A. Sungpet et al. state in an article entitled "Separation of Ethylene from Ethane Using Perfluorosulfonic Acid Ion-Exchange Membranes" published in ACS Symposium Series "Chemical Separations with Liquid Membranes," 270–285 (1996) that the selectivity and permeability of membranes for the separation of olefins from paraffins is too low to be attractive, so membranes have been combined with other separation processes to achieve the desired separation. We believe that the combination of membranes with distillation is also attractive for another reason: it allows for the maximum use of the vast amount of installed distillation capacity for the purification of olefins.

One of the first studies to examine the combination of facilitated transport membranes with distillation for the separation of olefins and paraffins was published by D. Gottschlich and D. Roberts in a paper for SRI Project 6519 and DOE Contract Number DE-AC07–76ID01570 entitled "Energy Minimization of Separation Process Using Conventional/Membrane Systems" (1990). They examined the application of a facilitated transport membrane to the bottom of a distillation column for the separation of propylene and propane. Since propylene (the olefin) is both the preferentially permeating component and the light component present in low concentration at the bottom of the column, this option appears unattractive because the low driving force leads to very large membrane areas.

Work by R. Noble and co-workers in two articles entitled "Analysis of a Membrane/Distillation Column Hybrid Process" published in J. Memb. Sci. 93, 31–44 (1994) and "Design Methodology for a Membrane/Distillation Column Hybrid Process" published in J. Memb. Sci. 99, 259–272 (1995) examined the design and optimization of several combined facilitated transport membrane and distillation processes for the separation of propylene and propane. Their work focused on the placement of the membrane around the distillation column in order to obtain an efficient process that accomplished the desired separation. They concluded that placing the facilitated transport membrane on the top of the column was preferred since this location takes advantage of the high propylene driving force (due to high propylene concentration).

Earlier work described in U.S. Pat. No. 5,057,641 in the names of Ronald J. Valus et al. and published by J. Davis et al. in an article entitled "Facilitated Transport Membrane Hybrid Systems for Olefin Purification" published in Sep. Sci. Tech 28, 463–476 (1993) also described placing a facilitated transport membrane on the top of a distillation column. This work also described the placement of a facilitated transport membrane on the sidedraw of a distillation column.

The work with silver-based facilitated transport membranes begun by R. Hughes described in U.S. Pat. No. 3,758,603 in 1973 continues today. However, an article recently published by A. Morisato et al. entitled "Transport properties of PA12-PTMO/AgBF4 solid polymer electrolyte membranes for olefin/paraffin separation" in Desalination 145, 347–351 (2002) indicates that the application of facilitated transport membranes continues to encounter difficulties including poor chemical stability due to carrier poisoning.

Advances in polymer membranes make them attractive candidates for olefin/paraffin separations since they do not depend on easily poisoned metal complexes to achieve the separation. For example, R. Burns and W. Koros present several polymeric materials that could be used for the separation of propylene and propane in a recent article entitled "Defining the Challenges for C3H6/C3H8 Separation Using Polymeric Membranes," J. Memb. Sci. 211, 299–309 (2003).

For polymeric membranes, a large pressure gradient across the membrane would supply the driving force for permeation. This driving force would induce a cooling in the membrane (for materials with positive Joule-Thomson coefficients) in order to produce the low pressure permeate. This affect is not present in facilitated transport membranes and has not been incorporated in previous processes based on them.

Little attention has been given to the heat balance around the membrane apparatus in the general membrane community, primarily because components previously considered for membrane based separations (nitrogen, oxygen, carbon dioxide, methane, hydrogen) are fixed gases. As membrane separations are examined for components that can exist both as a liquid and a vapor at typical industrial process conditions, there is a need to understand the effects of phase transformations on the performance of membrane apparatus.

There is, therefore, a present need for processes and apparatus using perm-selective membranes to provide heat integrated membrane apparatus where pressure-driven (fugacity-driven) membranes have been integrated with other processing steps for the separation of mixtures.

Improved apparatus should provide for an integrated sequence, carried out with streams in gas and/or liquid state, using a suitable perm-selective membrane, preferably a solid perm-selective membrane which under a suitable differential of a driving force exhibits selective permeability of a desired product, i.e., incorporate pressure-driven (fugacity-driven) membranes with existing separation assets.

SUMMARY OF THE INVENTION

In broad aspect, the present invention is directed to integrated distillation and membrane separation apparatus and uses thereof for economical separation of fluid mixtures.

More particularly, this invention relates to apparatus comprising a fractional distillation column and membrane device comprising a solid perm-selective membrane which are in flow communication. Advantageously apparatus of the invention is employed for simultaneous recovery of a very pure permeate product and another desired product from a mixture containing organic compounds.

This invention contemplates the treatment of a fluid feedstock, e.g. various type organic materials, especially a fluid mixture of compounds of petroleum origin. In general, the fluid feedstock is a gaseous mixture comprising a more selectively permeable component and a less permeable component. Apparatus of the invention are particularly useful in processes for treatment of a gaseous mixture comprised of a more selectively permeable alkene component and a corresponding alkane component, e.g. the separation of propylene from propane.

In one aspect, the invention provides integrated separation apparatus including a fractional distillation column and at least one perm-selective membrane device particularly suitable for simultaneous recovery of a very pure permeate product and another product from a fluid mixture of two or more compounds having different boiling point temperatures. The apparatus comprises: a fractional distillation column having an overhead vapor outlet in flow communication with a compressor, and internal or external heat transfer surface one side of which is disposed to contact fluid at the bottom of the column and the opposite side to contact compressed overhead vapor; a compressor in flow communication with a means for proportioning compressed vapor between the column heat transfer surface, a column reflux condenser, and a membrane cooler which cooler is in flow communication with a perm-selective membrane device; a membrane device comprising a solid perm-selective membrane which under a suitable differential of a driving force exhibits a permeability of at least 0.1 Barrer, channels having at least one inlet and one outlet for flow of fluid in contact with one side of a membrane, and contiguous with the opposite side thereof a permeate chamber having at least one outlet for flow of permeate; and means for flow communication between the opposite side of the column heat transfer surface and the fractional distillation column.

For the purposes of the present invention, the term "membrane device" is defined as any piece of equipment or apparatus designed to utilize a perm-selective membrane to separate one or more components from a fluid mixture of two or more compounds. The means for collection and/or distribution of fluid into the channel inlets of the membrane device, advantageously comprises a compressor and/or pump, preferably a compressor.

Depending on the separation required to simultaneously recover a very pure permeate product and another product from feed streams in a particular application, preferred embodiments of integrated separation apparatus according to the invention further comprise means for flow communication between the channel outlets of the membrane device and the fractional distillation column.

In another aspect, this invention provides a process for separation of purified products from a fluid mixture by utilization of an integrated fractional distillation and perm-selective membrane separation apparatus, which process comprises: providing an integrated separation apparatus comprising a fractional distillation column and membrane device designed to utilize a perm-selective membrane to separate one or more components from a fluid mixture of two or more compounds; withdrawing from the column a fluid stream derived by fractional distillation from a feedstock comprising two or more compounds having different boiling point temperatures; distributing all or portion of the stream withdrawn from the column into a membrane device to separate from the stream permeate and non-permeate fluids containing different amounts of at least one of the compounds; and controlling enthalpy to maintain the Membrane Efficiency Index of the non-permeate fluid within a suitable range, e.g., from about 0.5 to about 1.

For the purposes of the present invention, "Membrane Efficiency Index" (MEI) is defined as a ratio of the difference between the specific enthalpy of the feed stream entering the membrane device and specific enthalpy of the non-permeate fluid effluent to the difference between said specific enthalpy of the feed stream and the bubble point specific enthalpy of the non-permeate fluid at the non-permeate product pressure and composition.

Preferred processes utilizing integrated separation apparatus according to the invention control enthalpy to maintain MEI within a range of from about 0.5 to about 1.5, more preferably within a range of from about 0.7 to about 1.1, and most preferably within a range of from about 0.8 to about 1.05 for best results. Preferably the fluid withdrawn from the column is substantially vapor, and least a portion of the non-permeate fluid is returned to the column substantially as liquid.

Depending on the separations required, processes according to the invention shall further comprise withdrawing a purified permeate stream from the membrane device, and one or more purified product streams from the fractional distillation column, e.g., wherein the predominate component of the purified permeate fluid is propylene. Beneficially, the fluid stream withdrawn from the fractional distillation column is a substantially vapor overhead stream, a portion of which is utilized as a source of liquid reflux for the column.

In another aspect, the invention provides a process for separation of purified products from a fluid mixture by utilization of an integrated distillation and membrane separation apparatus which process comprises: providing separation apparatus comprising a fractional distillation column having suitable stages for vapor-liquid contacting, inlets and outlets including at least one outlet in flow communication with a membrane device comprising a plurality of solid perm-selective membranes which under a suitable differential of a driving force exhibit a permeability of at least 0.1 Barrer, channels having at least one inlet and one outlet for flow of fluid in contact with one side of a membrane, and contiguous with the opposite side thereof a permeate chamber having at least one outlet for flow of permeate; separating by fractional distillation a feedstock comprising a fluid mixture including a low-boiling component and a high-boiling component, and thereby provide to a column effluent enriched in one component relative to another; distributing a stream of the column effluent directly, or indirectly derived therefrom, into the channel inlets of the membrane device; and separating the distributed stream by means of selective permeation to thereby provide a purified permeate fluid and a non-permeate fluid while controlling enthalpy of the distributed stream to maintain Membrane Efficiency Index of the non-permeate fluid within a range from about 0.5 to about 1.5.

Depending on the separations required the separation apparatus further comprises means for apportioning an overhead vapor effluent into at least a first portion for reflux to the fractional distillation column and a second portion, and means for utilizing the first portion as liquid reflux. Advantageously, the second portion is distributed into the channel inlets of the membrane device.

In preferred embodiments of the invention at least a portion of the non-permeate fluid is returned to the fractional distillation column, and/or include a step of withdrawing from the column a purified distillation product enriched in one component relative to another component of the feedstock.

Processes of the invention are particularly suitable for separation of purified products from feedstock which comprises a mixture of an alkane compound having from 2 to about 4 carbon atoms and an alkene compound having the same number of carbon atoms as the predominate component of the feedstream. Advantageously the mixture has a liquid volume ratio of the alkene to the alkane compounds, and ratio is in a range of from about 1.5 to about 4.0.

Processes of the invention are particularly useful in treatment of fluid mixture comprised of a more selectively permeable alkene component and a corresponding alkane component, e.g. the separation of propylene from propane. Preferably the purified permeate stream comprises at least 90 percent propylene, more preferably the level of propylene in the purified permeate stream is at least 95 percent propylene, and most preferably at least 99.5 percent propylene.

In yet another aspect, the invention provides a process for separation of purified products from a fluid mixture by utilization of an integrated distillation and membrane separation apparatus which process comprises: providing separation apparatus comprising (a) a fractional distillation column having an overhead vapor outlet in flow communication with a compressor, and internal or external heat transfer surface one side of which is disposed to contact fluid at the bottom of the column and the opposite side to contact compressed overhead vapor, (b) a compressor in flow communication with a means for proportioning compressed vapor between the column heat transfer surface, a column reflux condenser, and a membrane cooler which cooler is in flow communication with a perm-selective membrane device, (c) a membrane device comprising a solid perm-selective membrane which under a suitable differential of a driving force exhibits a permeability of at least 0.1 Barrer, channels having at least one inlet and one outlet for flow of fluid in contact with one side of a membrane, and contiguous with the opposite side thereof a permeate chamber having at least one outlet for flow of permeate, and (d) means for flow communication between the opposite side of the column heat transfer surface and the fractional distillation column; separating by fractional distillation a feedstock comprising a fluid mixture including a low-boiling component and a high-boiling component, and thereby provide vapor stream enriched in the low-boiling component to the compressor; compressing the overhead vapor and distributing portions thereof between the column heat transfer surface, the column reflux condenser, and directly or indirectly the perm-selective membrane device; and separating from the stream distributed into the membrane device a non-permeate stream by means of selective permeation while controlling enthalpy of the distributed stream to maintain Membrane Efficiency Index of the non-permeate fluid within a range from about 0.5 to about 1.5.

Depending on the separations required, processes according to the invention shall further comprise withdrawing from the column a purified distillation product enriched in one component relative to another component of the feedstock, and/or withdrawing from the column a purified distillation product enriched in the low-boiling component relative to the feedstock. Advantageously at least a portion of the non-permeate fluid is returned to the fractional distillation column. Optionally, the apparatus may further comprises means for distribution of a "sweep" stream into the permeate chambers, but typically no sweep is required.

This invention is particularly useful towards separations involving organic compounds, in particular compounds which are difficult to separate by conventional means such as fractional distillation alone. Typically, these include organic compounds are chemically related as for example alkanes and alkenes of similar carbon number.

For a more complete understanding of the present invention, reference should now be made to the embodiments illustrated in greater detail in the accompanying drawing and described below by way of examples of the invention.

BRIEF DESCRIPTION OF THE DRAWINGS

The invention is hereinafter described in detail with reference to the accompanying drawings which are schematic flow diagrams depicting preferred aspects of the integrated fractional distillation and membrane separation processes and apparatus of the present invention for simultaneous recover of a very pure permeate product, an integrated non-permeate stream, and one or more desired product stream from the distillation column.

GENERAL DESCRIPTION

Figure 1:
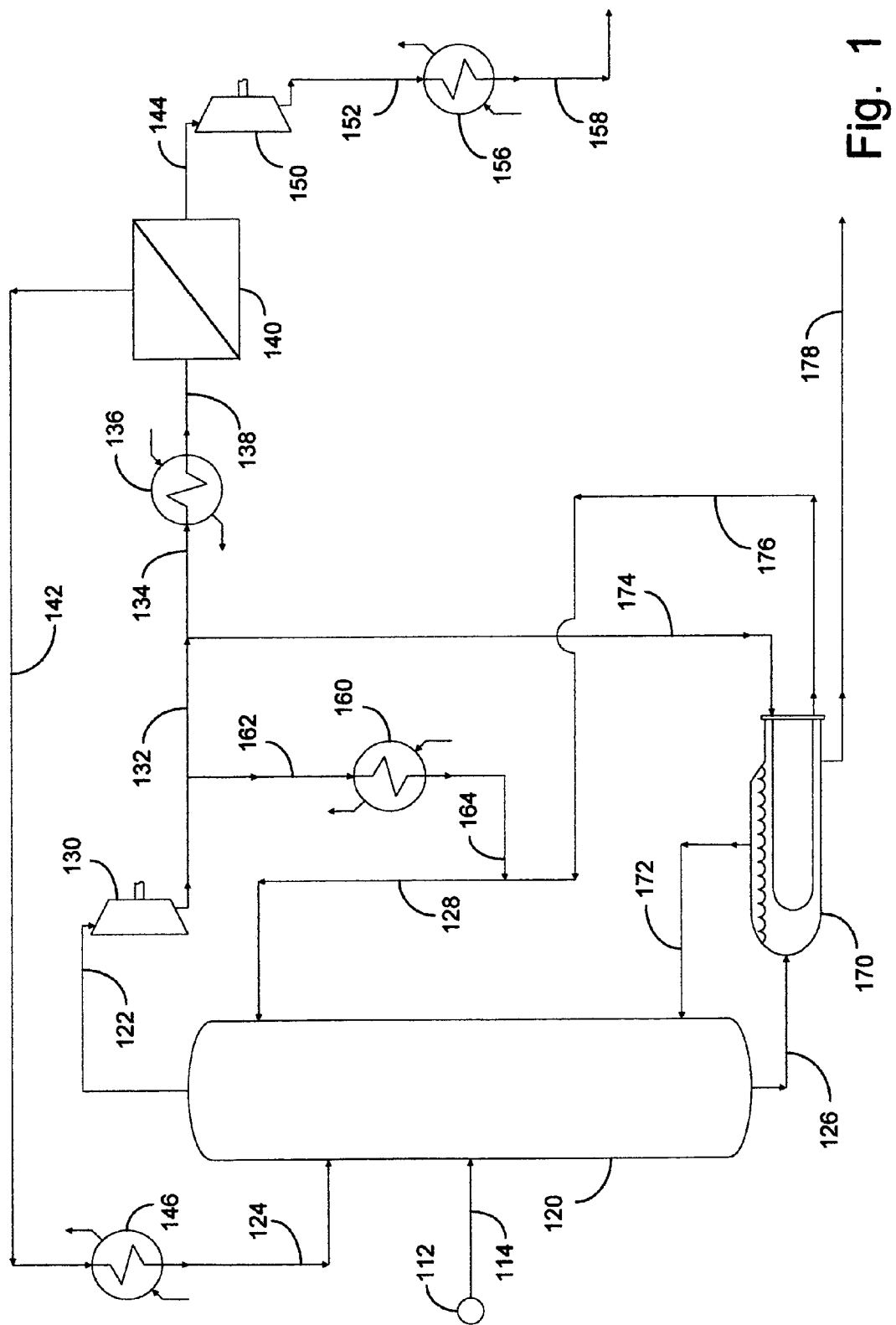
FIG. 1 is schematic drawing showing an embodiment of the present invention in which overhead vapor from a fractional distillation column is compressed and apportioned to provide streams for the membrane separation, heat for the column reboiler and return of liquid reflux to the column.

Any solid perm-selective membrane which under a suitable differential of a driving force exhibits a permeability and other characteristics suitable for the desired separations may be used according to the invention. Suitable membranes may take the form of a homogeneous membrane, a composite membrane or an asymmetric membrane which, for example may incorporate a gel, a solid, or a liquid layer. Widely used polymers include silicone and natural rubbers, cellulose acetate, polysulfones and polyimides.

Preferred membranes for use in vapor separation embodiments of the invention are generally of two types. The first is a composite membrane comprising a microporous support, onto which the perm-selective layer is deposited as an ultra-thin coating. Composite membranes are preferred when a rubbery polymer is used as the perm-selective material. The second is an asymmetric membrane in which the thin, dense skin of the asymmetric membrane is the perm-selective layer. Both composite and asymmetric membranes are known in the art. The form in which the membranes are used in the invention is not critical. They may be used, for example, as flat sheets or discs, coated hollow fibers, spiral-wound modules, or any other convenient form.

The driving forces for separation of vapor components by membrane permeation include, predominately their partial pressure difference between the first and second sides of the membrane. The pressure drop across the membrane can be achieved by pressurizing the first zone, by evacuating the second zone, introducing a sweep stream, or any combination thereof.

The membranes used in each group of modules may be of the same type or different. Although both units may contain membranes selective to the desired component to be separated, the selectivities of the membranes may be different. For example, where intermediate modules process the bulk of the fluid feedstock, these modules may contain membranes of high flux and moderate selectivity. The module group which deals with smaller streams, may contain membranes of high selectivity but lower flux. Likewise the intermediate modules may contain one type of membrane, and product modules may contain another type, or all three groups may contain different types. Useful embodiments are also possible using membranes of unlike selectivities in the intermediate modules and product modules.

Suitable types of membrane modules include the hollow-fine fibers, capillary fibers, spiral-wound, plate-and-frame, and tubular types. The choice of the most suitable membrane module type for a particular membrane separation must balance a number of factors. The principal module design parameters that enter into the decision are limitation to specific types of membrane material, suitability for high-pressure operation, permeate-side pressure drop, concentration polarization fouling control, permeability of an optional sweep stream, and last but not least costs of manufacture.

Hollow-fiber membrane modules are used in two basic geometries. One type is the shell-side feed design, which has been used in hydrogen separation systems and in reverse osmosis systems. In such a module, a loop or a closed bundle of fibers is contained in a pressure vessel. The system is pressurized from the shell side; permeate passes through the fiber wall and exits through the open fiber ends. This design is easy to make and allows very large membrane areas to be contained in an economical system. Because the fiber wall must support considerable hydrostatic pressure, the fibers usually have small diameters and thick walls, e.g. 100 µm to 200 µm outer diameter, and typically an inner diameter of about one-half the outer diameter.

A second type of hollow-fiber module is the bore-side feed type. The fibers in this type of unit are open at both ends, and the feed fluid is circulated through the bore of the fibers. To minimize pressure drop inside the fibers, the diameters are usually larger than those of the fine fibers used in the shell-side feed system and are generally made by solution spinning. These so-called capillary fibers are used in ultra-filtration, pervaporation, and some low- to medium-pressure gas applications.

Concentration polarization is well controlled in bore-side feed modules. The feed solution passes directly across the active surface of the membrane, and no stagnant dead spaces are produced. This is far from the case in shell-side feed modules in which flow channeling and stagnant areas between fibers, which cause significant concentration polarization problems, are difficult to avoid. Any suspended particulate matter in the feed solution is easily trapped in these stagnant areas, leading to irreversible fouling of the membrane. Baffles to direct the feed flow have been tried, but are not widely used. A more common method of minimizing concentration polarization is to direct the feed flow normal to the direction of the hollow fibers. This produces a cross-flow module with relatively good flow distribution across the fiber surface. Several membrane modules may be connected in series, so high feed solution velocities can be used. A number of variants on this basic design have been described, for example U.S. Pat. No. 3,536,611 in the name of Fillip et al., U.S. Pat. No. 5,169,530 in the name of Sticker et al., U.S. Pat. No. 5,352,361 in the name of Parsed et al., and U.S. Pat. No. 5,470,469 in the name of Beckman which are incorporated herein by reference each in its entirety. The greatest single advantage of hollow-fiber modules is the ability to pack a very large membrane area into a single module.

DESCRIPTION OF THE PREFERRED EMBODIMENTS

Figure 2:
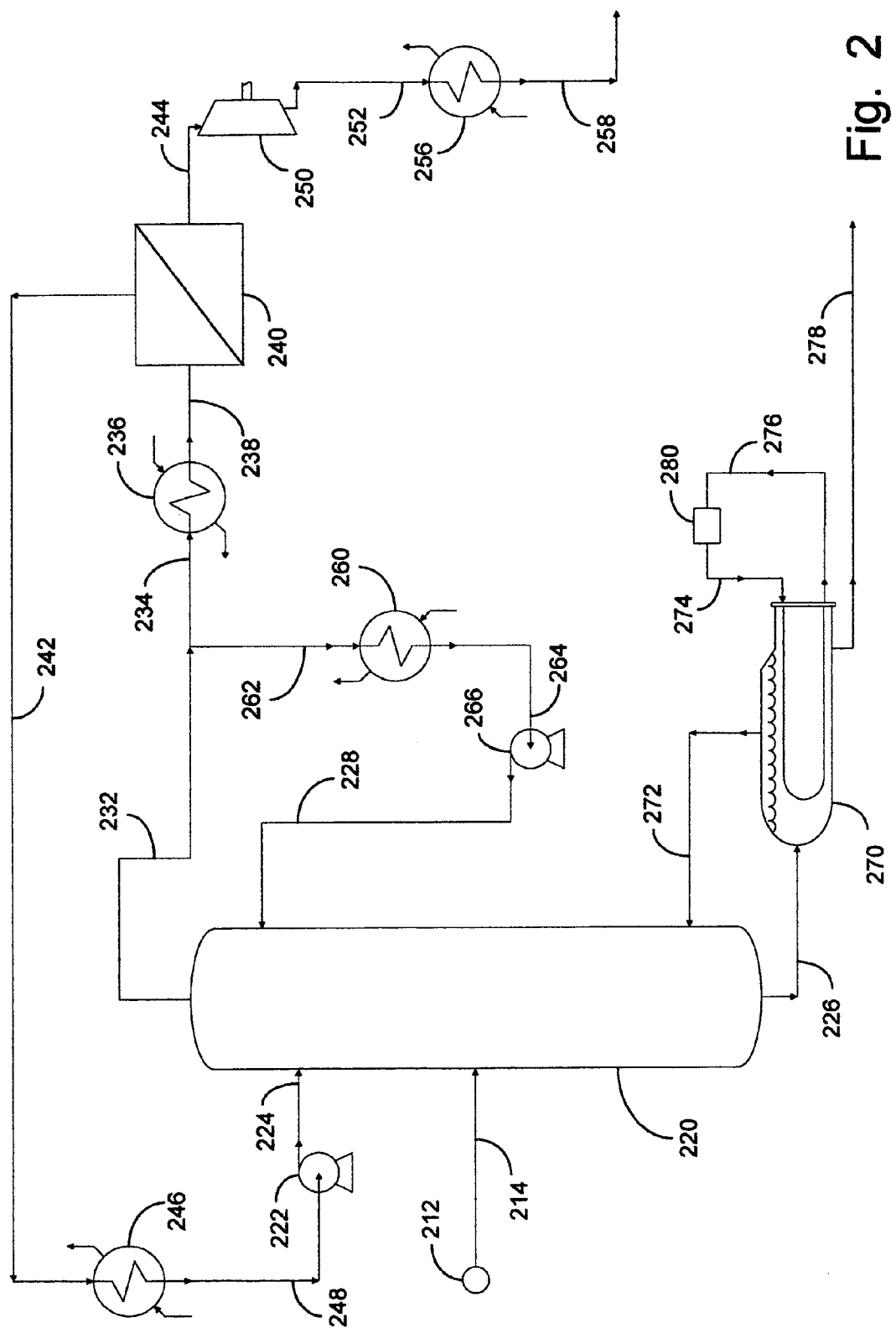
FIG. 2 is schematic drawing showing an embodiment of the present invention in which overhead vapor from a fractional distillation column is apportioned to provide streams for the membrane separation and return of liquid reflux to the column, without compression of overhead vapor from a fractional distillation column.
Figure 3:
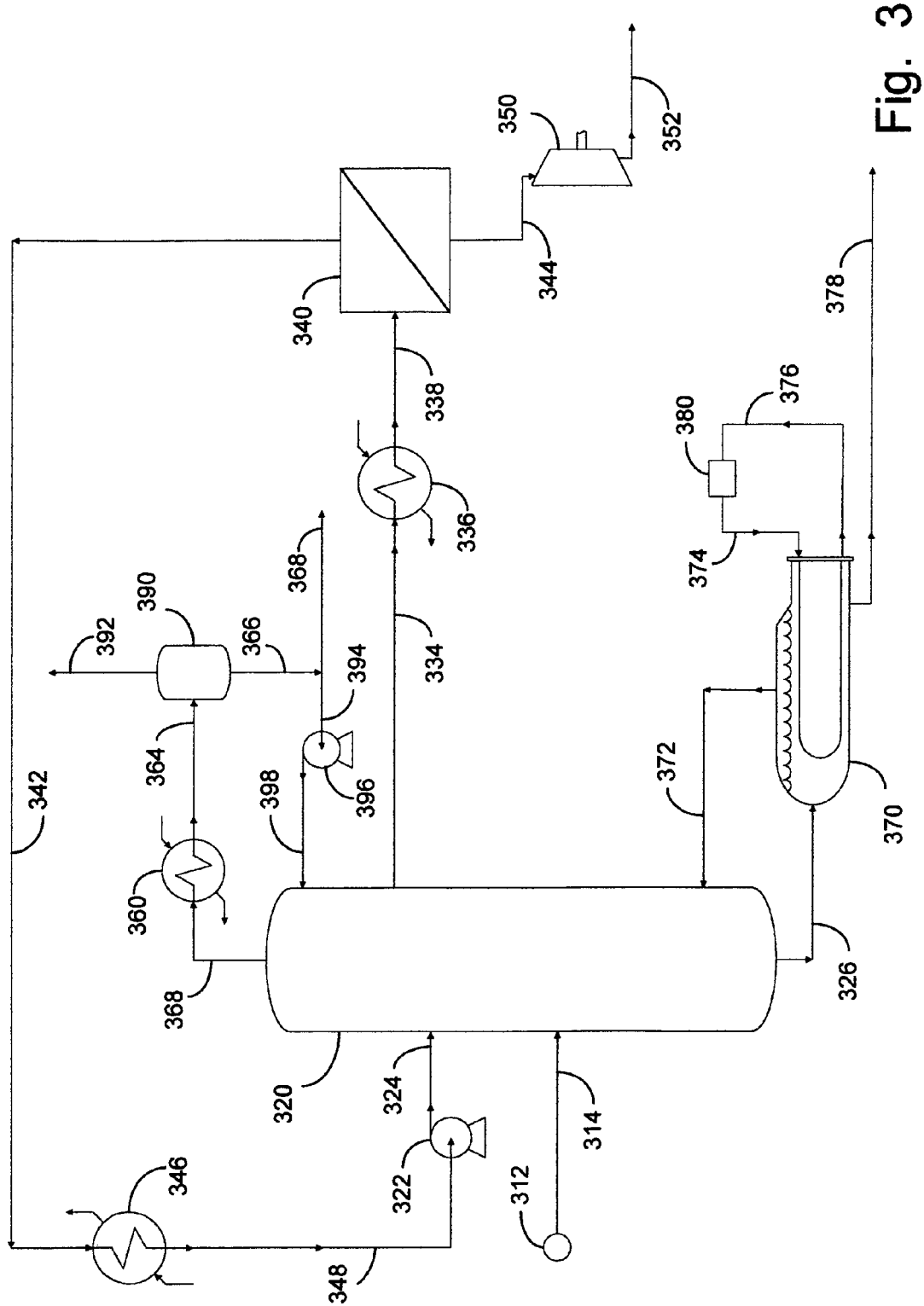
FIG. 3 is schematic drawing showing an embodiment of the present invention in which a fluid stream for membrane separation is a sidedraw from a fractional distillation column thereby obtaining a very pure permeate product, an integrated non-permeate stream, and desired product streams from the distillation column.

In order to better communicate the present invention, several preferred aspects of the integrated fractional distillation and membrane separation processes and apparatus of the present invention for simultaneous recover of a very pure permeate product, an integrated non-permeate stream, and one or more desired products of the distillation are depicted schematically in FIG. 1, FIG. 2, and FIG. 3. In these preferred embodiments of the invention, the distillation feedstock is a mixture comprising a more selectively permeable alkene component and a corresponding alkane component, for example propane and propene (propylene). Other examples of light hydrocarbon compounds which are difficult to separate by traditional separation methods, such as fractional distillation, are shown in Table I.

TABLE I

NORMAL BOILING POINT TEMPERATURES OF LIGHT HYDROCARBON COMPOUNDS

| HEAVY HYDROCARBON | B.P. ° C. | LIGHT HYDROCARBON | B.P. ° C. |
|---|---|---|---|
| Ethane | −88.5 | Ethene (ethylene) | −102.4 |
| Propane | −42.2 | Propene (propylene) | −47.7 |
| Propadiene | −34.5 | Propane | −42.2 |
| Butane | −0.6 | Methylpropene (isobutylene) | −6.6 |
| Butane | −0.6 | 1-Butene (α-butylene) | −6.47 |
| Butane | −0.6 | 1,3-Butadiene | −4.75 |
| 2-Butene (β-butylene) | 3.73 | Butane | −0.6 |
| n-Butane | −0.6 | iso-Butane | −12 |
| 1-Butene (α-butylene) | −6.47 | Methylpropene (isobutylene | −6.6 |
| 2-Butene (β-butylene) | 3.73 | Methylpropene (isobutylene | −6.6 |

Configuration of the integrated fractional distillation column and membrane separation modules for a particular separation depends on many factors. These factors include (1) the concentration of the desired component in the feed stream; (2) the physical and chemical properties of the components being separated; (3) the required purity of the product streams; (4) the relative values of the products, which determines acceptable recovery; (5) the tradeoff between membrane capital cost and the cost of pumping or compression; and (6) how the membrane is integrated with other processing steps. In the separation of mixtures using integrated fractional distillation and membrane separation, the required product recoveries and product purity must be achieved at acceptable capital and operating costs. For the purposes of the present invention, the term "membrane separation module" is defined as a plurality of perm-selective membranes, disposed to form a membrane device.

Referring now to FIG. 1, in which fractional distillation column 120 and a membrane separation device 140 are disposed according to a preferred aspect of the invention. Feedstock comprising two or more compounds having different boiling point temperatures, flows from a source 112 through conduit 114, and, depending on the operating conditions employed in a particular application, an optional pump or vaporizer and compressor (not shown), into fractional distillation column 120. According to this embodiment of the invention, the more selectively permeable component of the feedstock has a low boiling point temperature relative to other compounds in the feedstock. Such aspects of the invention are particularly useful in processes for treatment of a fluid mixture comprised of a more selectively permeable alkene component and a corresponding alkane component, e.g. the separation of purified products from a mixture of propylene and propane.

An overhead vapor stream, at or above dew point conditions thereof, is transferred to inlet of compressor 130 through conduit 122, and a compressed effluent having higher enthalpy than the overhead vapor is distributed though manifold 132. A portion of the compressed effluent is distributed into membrane device 140 through conduit 134, cooling exchanger 136, and conduit 138. Exchanger 136 is designed and operated as a means to control the enthalpy of the stream distributed into membrane device 140.

As required to provide suitable liquid reflux for the fractional distillation, another portion of the compressed effluent is distributed from manifold 132 into condenser 160 through conduit 162. Liquid from condenser 160 is returned to the top of fractional distillation column 120 through conduit 164 and reflux manifold 128. Condenser 160 is designed and operated to condense and sub-cool the stream condensate therefrom flowing into reflux manifold 128.

As shown in this embodiment, the balance of the compressed effluent is distributed into an internal coil of reboiler 170 through conduit 174, and liquid condensate therefrom is returned to fractional distillation column 120 through conduit 176 and reflux manifold 128. Liquid from the bottom of fractional distillation column 120 is supplied to reboiler 170 through conduit 126, and vapor therefrom is returned to the bottom of fractional distillation column 120 through conduit 172. A purified high-boiling product is withdrawn from reboiler 170 through conduit 178, and transferred to storage (not shown).

Non-permeate fluid from membrane device 140 is returned to fractional distillation column 120 through conduit 142, optional exchanger 146, and conduit 124. According to this embodiment of the invention, cooperation and interaction between aspects of fractional distillation and perm-selective membrane separation beneficially operate to control enthalpy of the compressed effluent distributed into membrane device, thereby maintaining the Membrane Efficiency Index of the non-permeate fluid from membrane device 140 within a range from about 0.5 to about 1.5, preferably within a range from about 0.7 to about 1.1, and more preferably within a range from about 0.8 to about 1.05. A stream of purified permeate comprising the more selectively permeable component of the overhead vapor, flows from membrane device 140 into compressor 150, or an alternative vacuum system, (not shown) through conduit 144, and therefrom through conduit 152, cooling exchanger 156, and conduit 158 to purified product storage (not shown).

Referring now to FIG. 2, in which fractional distillation column 220 and a membrane separation device 240 are disposed according to another preferred aspect of the invention. Feedstock comprising two or more compounds having different boiling point temperatures, flows from a source 212 flows through conduit 214, and into fractional distillation column 220. According to this embodiment of the invention, the more selectively permeable component of the feedstock has a low boiling point temperature relative to other compounds in the feedstock. This aspects of the invention is particularly useful in treatment of a fluid mixture comprised of a more selectively permeable alkene component and a corresponding alkane component, e.g. the separation of purified products from a mixture of propylene and propane.

An overhead vapor stream is transferred form the top of fractional distillation column 220 though manifold 232. A portion of the overhead vapor stream is distributed into membrane device 240 through conduit 234, cooling exchanger 236, and conduit 238. As required to provide suitable liquid reflux for the fractional distillation, a suitable portion of the overhead vapor stream is distributed from manifold 232 into condenser 260 through conduit 262. Liquid from condenser 260 is returned to the top of fractional distillation column 220 through conduit 264, reflux pump 266 and conduit 228.

Liquid from the bottom of fractional distillation column 220 is supplied to reboiler 270 through conduit 226, and vapor therefrom is returned to the bottom of fractional distillation column 220 through conduit 272. In this embodiment, an internal coil of reboiler 270 is supplied with steam from source 280 through conduit 274, and liquid condensate therefrom is returned to steam source 280 through conduit 276. A purified high-boiling product is withdrawn from reboiler 270 and transferred to storage (not shown) through conduit 278.

Non-permeate fluid from membrane device 240 flows into optional exchanger 246 through conduit 224, and returns to fractional distillation column 220, by means of conduit 248 and pump conduit 222, through conduit 242. According to this embodiment of the invention, cooperation and interaction between aspects of fractional distillation and perm-selective membrane separation beneficially operate to control enthalpy of the fluid distributed into membrane device, thereby maintaining the Membrane Efficiency Index of the non-permeate fluid from membrane device 240 within a range from about 0.5 to about 1.5, preferably within a range from about 0.7 to about 1.1, and more preferably within a range from about 0.8 to about 1.05. A stream of purified permeate comprising the more selectively permeable component of the overhead vapor, flows from membrane device 240 into compressor 250, or an alternative vacuum system, (not shown) through conduit 244, and therefrom through conduit 252, cooling exchanger 256, and conduit 258 to purified permeate storage (not shown).

Referring now to FIG. 3, in which fractional distillation column 320 and a membrane separation device 340 are disposed according to another preferred aspect of the invention. In this embodiment of the invention, the feedstock comprises two or more compounds having different boiling point temperatures and at least one other light compound which does not permeate the membrane. Such aspects of the invention are particularly useful in processes for treatment of a fluid mixture comprised of a more selectively permeable alkene component, a corresponding alkane component having the same number of carbon atoms, and hydrocarbons having less carbon atoms, e.g. the separation of purified products from a mixture of propylene and propane which also contains a lesser amount of ethane and/or ethylene.

Feedstock, flows from a source 312 through conduit 314, and into fractional distillation column 320. An overhead gaseous stream is transferred form the top of fractional distillation column 320 though conduit 368, overhead condenser 360 and conduit 364 into knockout drum 390. A gaseous stream containing non-condensed compounds is vented from knockout drum 390 through conduit 392 for another use, storage, and/or disposal (not shown). Condensate is withdrawn from knockout drum 390 through manifold 366. As required to reflux the fractional distillation, a portion of the condensate is returned to the top of column 320 by means of conduit 394, reflux pump 396 and conduit 398. A stream of purified overhead product is transferred to storage (not shown) through conduit 368.

A fluid sidedraw stream is withdrawn from fractional distillation column 320 through conduit 334, located between the top of the column and feed conduit 314. The sidedraw stream is distributed into membrane device 340 through heat exchanger 336 and conduit 338. Exchanger 336 is designed and operated as a means to control the enthalpy of the stream distributed into membrane device 340. According to this embodiment of the invention, the more selectively permeable component of the feedstock has a low boiling point temperature relative to other condensable compounds in the feedstock. Non-permeate fluid from membrane device 340 is returned to fractional distillation column 320 through conduit 342, optional exchanger 346, conduit 348, pump 322 and conduit 324.

Liquid from the bottom of fractional distillation column 320 is supplied to reboiler 370 through conduit 326, and vapor therefrom is returned to the bottom of fractional distillation column 320 through conduit 372. In this embodiment, an internal coil of reboiler 370 is supplied with steam from source 380 through conduit 374, and liquid condensate therefrom is returned to steam source 380 through conduit 376. A purified high-boiling product is withdrawn from reboiler 370 and transferred to storage (not shown) through conduit 378.

According to this embodiment of the invention, cooperation and interaction between aspects of fractional distillation and perm-selective membrane separation beneficially operate to control enthalpy of the compressed effluent distributed into membrane device, thereby maintaining the Membrane Efficiency Index of the non-permeate fluid from membrane device 340 within a range from about 0.5 to about 1.5, preferably within a range from about 0.7 to about 1.1, and more preferably within a range from about 0.8 to about 1.05. A stream of purified permeate comprising the more selectively permeable component of the overhead vapor, flows from membrane device 340 into compressor 350, or an alternative vacuum system, (not shown) through conduit 344, and therefrom through conduit 352, to purified permeate storage (not shown).

EXAMPLES OF THE INVENTION

The following examples will serve to illustrate certain specific embodiments of the herein disclosed invention.

These Examples should not, however, be construed as limiting the scope of the novel invention as there are many variations which may be made thereon without departing from the spirit of the disclosed invention, as those of skill in the art will recognize.

General

These examples demonstrate critical aspects of preferred processing configurations utilizing fugacity-driven membranes which are integrated with other processing steps for the separation of mixtures of propylene and propane. More particularly according to the invention, such apparatus includes a perm-selective membrane device used in cooperation with a fractional distillation column for simultaneous recovery of a very pure permeate product and a desired non-permeate product from a propane-propylene feedstock. The examples include the results of computer calculations, performed using commercially available chemical process modeling programs (e.g. Aspen Plus from Aspen Technology, Inc.) where models of membranes have been incorporated with standard chemical process equipment models. The models of membranes were developed by BP and based on generally accepted gas permeation equations. (See Shindo et al., "Calculation Methods for Multicomponent Gas Separation by Permeation," *Sep. Sci. Technol.* 20, 445–459 (1985), Kovvali et al., "Models and Analyses of Membrane Gas Permeators," *J. Memb. Sci.* 73, 1–23 (1992), and Coker et al., "Modeling Multicomponent Gas Separation Using Hollow-Fiber Membrane Contactors," *AIChE J.* 44, 1289–1302 (1998).)

For the purposes of the present invention, the permeability of gases through membranes is measured in "Barrer", which is defined as $10^{-10}$ [cm$^3$ (STP) cm/(cm$^2$·sec·cm Hg)] and named after R. M. Barrer. Membrane permeability is a measure of the ability of a membrane to permeate a gas. The term "membrane selectivity" is defined as the ratio of the permeabilities of two gases and is a measure of the ability of a membrane to separate the two gases. (For example, see Baker, Richard W., "Membrane Technology and Applications", pp. 290–291, McGraw-Hill, New York, 2000).

All the calculations were conducted at a membrane permeate pressure of 40 psia. Permeate was compressed to a pressure where it could be condensed with 37.8° C. (100° F.) water (approximately 250 psia). In examples where significant subcooling of nonpermeate occurred within the membrane device, the amount of membrane area required to meet the permeate purity specifications rapidly increased with the amount of subcooling. Advantageously, according preferred processes of the invention, subcooling of nonpermeate within the membrane device is limited thereby beneficially controlling the required membrane area. Since fugacity of a liquid is a strong function of temperature, it appeared that the driving force rapidly decreased when the nonpermeate was subcooled.

The position where the nonpermeate recycle entered the column was chosen so the nonpermeate composition matched the composition of the material in the column at that position. This matched the key ratio of the nonpermeate to the key ratio in the column at that point, following rules of thumb published elsewhere (for example Kister, H. Z., "Distillation Design", McGraw Hill, 1992.)

Example 1

This example documents an aspect of the preferred embodiment of the invention depicted in FIG. 1. Fractional distillation column 120 was utilized as a C3 splitter with a portion of the compression overhead vapor advantageously distributed into a fugacity-driven membrane separation device 140. Calculations were made using 37.8° C. (100° F.) cooling water in condenser 160. Heat exchangers 136 and 146 were not employed in this example. A temperature gradient of 11.1° C. (20° F.) was assumed across the reboiler in order to set the pressure at the bottom of the column. A pressure drop of 0.1 psi per tray was assumed to determine the compressor suction conditions. This resulted in a column overhead pressure of approximately 140 psia. The liquid rate in the column was chosen so that the separation could be completed with 200 trays, a typical tray requirement for a C3 splitter, and the vapor rate was set so that the column bottoms product met the HD-5 Liquefied Petroleum Gas (LPG) specification of 5 percent propylene.

Before the membrane was placed on the apparatus, the column diameter and compressor were sized to process 10,000 barrels per day (BPD) of Refinery-Grade Propylene (RGP) containing 74 percent propylene and 26 percent propane from source 112 and produce an overhead product that met the Polymer-Grade Propylene (PGP) specification of 99.5 percent propylene.

In this example, the overall reflux ratio has been lowered and the overhead purity from the column decreased to adjust the membrane feed enthalpy and Membrane Efficiency Index. Since the capacity of the column and compressor would be too large once the reflux ratio was lowered, the feed rate to the column from source 112 was increased as reflux ratio was decreased to the point where the amount of material passing through overhead compressor 130 remained the same. Membranes (140) were employed to produce PGP from the lower purity overhead material. Calculations were performed using a membrane propylene permeability of 2 Barrer and a propylene selectivity of 15.

The results of these calculations are shown in Table 1. The membrane area was adjusted as the overhead purity was changed to produce permeate that met PGP specifications. Membrane cooling was insufficient at less than about 98 percent propylene in the overhead to completely (desuperheat and) condense the nonpermeate, and a vapor-liquid mixture was recycled to the column. Above 98 percent propylene in the overhead when the nonpermeate flow rate was not as high, membrane cooling caused the nonpermeate to be subcooled. Note that some of the liquid in the higher-pressure nonpermeate was also vaporized when it entered the column at 140–160 psia, even when the nonpermeate was subcooled. Table 1 shows that the amount of material that could be processed increased until an overhead propylene content of about 98 percent was reached. Below about 98 percent propylene in the overhead, the amount of nonpermeate being recycled to the column started to increase significantly and the throughput of the apparatus decreased. This maximum in apparatus throughput occurred when the Membrane Efficiency Index was approximately 1.

TABLE I

DISTILLATION COLUMN WITH VAPOR COMPRESSION

| OVERHEAD PROPYLENE PERCENT BY VOLUME | MEI†† | THROUGHPUT INCREASE, PERCENT | NONPERMEATE DEGREES SUBCOOLED/ VAPOR FRACTION | RATIO OF NONPERMEATE TO COLUMN FEED | AREA, $ft^2 \times 10^{-3}$ |
|---|---|---|---|---|---|
| 99 | 1.02 | 12 | 35° F. | 0.004 | 255 |
| 98 | 1.00 | 22 | 18° F. | 0.04 | 271 |
| 97 | 0.65 | 19 | 0.7 | 0.2 | 248 |

††MEI is Membrane Efficiency Index.

According to the preferred embodiment of the invention depicted in FIG. 1, a membrane device is incorporated with a C3 splitter that employs vapor compression. Since the compressor discharge has a significantly higher pressure than the column, the membrane nonpermeate is recycled to the column without further pressurization and no expensive pressurization equipment was required.

Example 2

This example documents an aspect of the invention depicted in FIG. 1, utilizing optional heat exchangers 136 and 146 on the membrane feed and/or the nonpermeate in order to limit the amount of vapor being recycled to the column. In this example, calculations were performed at conditions similar to those of Example 1 using heat exchangers 136 and/or 146 on the membrane feed and/or the nonpermeate. It was necessary to cool the membrane feed to from 26.7° to 37.8° C. (80° to 100° F.) or the nonpermeate to approximately 21.1° C. (70° F.) to eliminate vapor recycle to the column. However, this had a small impact on the performance of this propane-propylene separation system. Note that the absolute flow rate of the nonpermeate did not change when heat exchangers 136 and 146 were employed because the nonpermeate flow rate is affected by the feed composition, feed rate, area, and perm-selectivity of the membrane. The heat exchangers affected the phase when the nonpermeate entered the column. A slight enhancement in throughput due to heat exchanger 146 was observed when the nonpermeate rate was high. Utilizing heat exchanger 136 produced similar results; however, heat exchanger 136 was significantly more expensive than heat exchanger 146 since the membrane feed has a larger flow rate than the nonpermeate. The membrane area required was also larger (up to 25 percent) when using heat exchanger 136 since cooling the membrane feed caused the nonpermeate to completely condense and subcool upon membrane cooling.

Note that the temperature of heat exchanger 146 in this example was approximately 21.1° C. (70° F.). In practice, cooling water would generally be insufficient for this service and another cooling source (e.g. refrigeration) would be required. The minimal throughput increases observed would not warrant the additional costs of employing heat exchangers 136 and 146 in this case.

Example 3

This example documents an aspect of the preferred embodiment of the invention depicted in FIG. 2. Fractional distillation column 220 was utilized as a C3 splitter with a portion of the overhead vapor advantageously distributed into a fugacity-driven membrane separation device 240. The nonpermeate effluent from separation device 240 was completely liquefied and pressurized by means of pump 222 for recycling into column 220. Calculations were made using 37.8° C. (100° F.) cooling water in condenser 260. This resulted in a column overhead pressure of approximately 230 psia. The liquid rate in the column was chosen so that the separation could again be completed with 200 trays. At the same time, the vapor rate in the column was set so that the column bottoms product met LPG specifications.

Before the membrane was placed on the apparatus, the existing column diameter was sized to process 10,000 BPD of RGP from source 212 containing 74 percent propylene and 26 percent propane feed. The overall reflux ratio has again been lowered and the overhead purity from the column decreased to adjust the membrane feed enthalpy and Membrane Efficiency Index. In this example, the feed rate to the column was increased as the reflux ratio was decreased to the point where the column vapor rate remained the same. Membranes (240) were employed to produce PGP from the lower purity overhead material. Calculations were performed using a membrane propylene permeability of 2 Barrer and a propylene selectivity of 15.

The results of these calculations are shown in Table 2. The membrane area was again adjusted to produce permeate that met PGP specifications. The amount of material that could be processed increased until an overhead propylene content of about 97–98 percent was reached. At less than approximately 97 percent propylene in the overhead, the amount of nonpermeate being recycled to the column started to increase significantly and the throughput of the apparatus decreased. This maximum in apparatus throughput again occurred when the Membrane Efficiency Index was approximately 1.

TABLE II

NONPERMEATE IS INTRODUCED INTO THE
DISTILLATION COLUMN THROUGH A PUMP

| OVERHEAD PROPYLENE, PERCENT BY VOLUME | MEI†† | THROUGHPUT INCREASE, PERCENT | EXCHANGER DUTY† | RATIO OF NONPERMEATE TO COLUMN FEED | MEMBRANE AREA, $ft^2 \times 10^{-3}$ |
|---|---|---|---|---|---|
| 99 | 1.03 | 15 | NA | 0.004 | 291 |
| 98 | 1.03 | 26 | NA | 0.04 | 298 |
| 97 | 0.76 | 26 | 1.0 | 0.2 | 272 |
| 96 | 0.43 | 25 | 6.2 | 0.5 | 271 |

††MEI is Membrane Efficiency Index.
†Duty is cooler 246 duty to condense non-permeate stream, BTU/Hr × $10^{-3}$.

When the column overhead propylene content was greater than approximately 98 percent, membrane cooling completely condensed (and subcooled) the nonpermeate and thus no cooler (246) was needed for the nonpermeate. Below about 98 percent, nonpermeate recycle was increased in order to make the permeate PGP specification and membrane cooling decreased enough so that the nonpermeate was not completely condensed. Cooler 246 was employed to completely condense the nonpermeate before sending it to the nonpermeate pump. Coincidentally in this example no further throughput increase was possible when cooler 246 was employed because nonpermeate recycle was beginning to decrease the apparatus fresh feed capacity. These results unexpectedly showed that in this case by accounting for the effect of membrane cooling in a heat integrated process it was possible to eliminate the nonpermeate cooler and the capital and operating costs associated with it.

The embodiment of the invention depicted in FIG. 2 is particularly preferred for cooperative integration of a membrane device with a conventional C3 splitter. Due to pressure drop in the membrane, it is necessary to pressurize the nonpermeate before recycling it to the column. The cost savings of this apparatus is very significant since it uses a pump and not a compressor to pressurize the nonpermeate, completely eliminating gas compression, which typically leads to high capital, operating, and maintenance costs.

Note that cooler 236 could also be used to ensure the nonpermeate recycle was completed liquefied after membrane cooling. However, utilizing cooler 236 would be more expensive than cooler 246 since cooler 236 would have to cool the membrane feed, which has a larger flow rate than the nonpermeate.

Example 4

In this example calculations performed in Example 3, but using a propylene selectivity of 35 and a propylene permeability of 1 Barrer. A higher propylene permeability was used when selectivity was lowered because it has been noted in the membrane literature (see for example Robeson, "Correlation of Separation Factor Versus Permeability for Polymeric Membranes," *J. Memb. Sci.* 62, 165–185 (1991) or Burns, R. L. et al., "Defining the Challenges for C3H6/C3H8 Separation Using Polymeric Membranes," *J. Memb. Sci.*, 211, 299–309 (2003)) that decreasing selectivity generally leads to higher values of permeability. The results of these calculations are shown in Table 3. More throughput increase was achieved for the apparatus shown in FIG. 2 when the selectivity of the membrane was higher. This illustrates that the apparatus shown in FIG. 2 is preferred even at a higher membrane selectivity. With higher propylene selectivity, the propylene concentration of the membrane feed and the reflux rate of the column could be lowered further before permeate recovery dropped and nonpermeate recycle became significant. More membrane area was required because the propylene permeability was lower. As in Example 3, it was possible to eliminate nonpermeate cooler 246 with little effect on throughput increase when membrane cooling was sufficient to completely condense the nonpermeate at a Membrane Efficiency Index of approximately 1.

TABLE III

NONPERMEATE IS INTRODUCED INTO THE
DISTILLATION COLUMN THROUGH A PUMP

| OVERHEAD PROPYLENE, PERCENT BY VOLUME | MEI†† | THROUGHPUT INCREASE, PERCENT | EXCHANGER DUTY† | RATIO OF NONPERMEATE TO COLUMN FEED | MEMBRANE AREA, $ft^2 \times 10^{-3}$ |
|---|---|---|---|---|---|
| 97 | 0.97 | 39 | NA | 0.03 | 730 |
| 96 | 0.98 | 43 | NA | 0.05 | 716 |
| 95 | 1.00 | 43 | 0.03 | 0.1 | 669 |
| 94 | 0.86 | 39 | 1.0 | 0.2 | 651 |

††MEI is Membrane Efficiency Index.
†Duty is cooler 246 duty to condense non-permeate stream, BTU/Hr × $10^{-3}$.

Example 5

This example documents an aspect of the preferred embodiment of the invention depicted in FIG. 3. Fractional distillation column 320 was utilized as a C3 splitter with a sidedraw stream advantageously distributed into a fugacity-driven membrane separation device 340. The nonpermeate effluent from separation device 340 was completely liquefied and pressurized by means of pump 322 for recycling into column 320. FIG. 3 shows an apparatus where a fugacity driven membrane has been placed on a sidedraw of a distillation column and the nonpermeate has been completely liquefied and pressurized with a pump before recycling back to the column.

Feedstock, from source 312, contained components having boiling point temperatures less than that of propylene. advantageously a desired propylene-rich side product is obtained while permitting light materials to leave the system via the column overhead. The feed from source 312 used here contained 3 wt. percent ethane, 69 wt. percent propylene, and 28 wt. percent propane. Ethane was chosen because it is a low boiler often present in the effluent of cracking processes used to produce propylene. It must be removed so that it does not end up in the propylene-rich and propane-rich products of the column. In this example, products were withdrawn only via conduits 392, 352, and 378. Calculations were made using cooling water at 37.8° C. (100° F.) to produce column reflux. This resulted in a column overhead pressure of approximately 320 psia. Calculations were performed for a column with 200 trays. The vapor sidedraw was drawn from tray 20 (numbered from the top.) The vapor rate in the column was again set so that the column bottoms product met LPG specifications. Membranes (340) were employed to produce PGP. Calculations were performed using a membrane propylene permeability of 2 Barrer and a propylene selectivity of 15.

The composition of the membrane feed has been decreased by increasing the rate of the vapor sidedraw in order to vary the Membrane Efficiency Index. The membrane area was again simultaneously adjusted to produce permeate that met PGP specifications. The results are shown in Table IV. For membrane feed propylene content of greater than about 96 percent, membrane cooling was sufficient to completely condense (and subcool) the nonpermeate and cooler 346 was not needed to liquefy the nonpermeate. As the membrane feed propylene content decreased below about 96 percent, nonpermeate recycle increased and membrane cooling was not sufficient to completely condense the nonpermeate, thereby requiring the use of cooler 346. This transition requiring the use of cooler 346 occurred when the Membrane Efficiency Index was approximately 1.

This example shows that the apparatus shown in FIG. 3 was the preferred way to incorporate a membrane on a column sidedraw when light components in the column feed would concentrate in the overhead product. For the purification of propylene, this apparatus could simultaneously deethanize and produce desired products like PGP and LPG. The use of a pump to pressurize the nonpermeate was preferred since it eliminated costly gas compression. Adjustment of the Membrane Efficiency Index again made it possible to eliminate the nonpermeate cooler and the capital and operating costs associated with it.

TABLE IV

DISTILLATION COLUMN SIDEDRAW FOR A PURIFIED PERMEATE OF 99.5 PERCENT PROPYLENE

| SIDEDRAW PROPYLENE, PERCENT | EXCHANGER 346 DUTY, BTU/Hr × ×10$^{-3}$ | MEI†† |
|---|---|---|
| 98 | N.A. | 1.01 |
| 97 | N.A. | 1.02 |
| 96 | 0.46 | 0.80 |

††MEI is Membrane Efficiency Index.

Example 6

This example documents an aspect of the preferred embodiment of the invention depicted in FIG. 3 by which means two desirable propylene-rich products and a desirable propane-rich product are simultaneously provided. The feedstock from source 312 was 10,000 BPD of RGP containing 74 percent propylene and 26 percent propane. Calculations were made using cooling water at 37.8° C. (100° F.) to completely condense the column overhead. This resulted in a column overhead pressure of approximately 230 psia. Calculations were performed for a column with 200 trays. The vapor sidedraw was drawn from tray 65 (numbered from the top.)

In this example, the reflux rate to the column was adjusted to produce an overhead liquid product (368) that met PGP specifications. The column sidedraw was sent to membrane module 340 and the membrane area was adjusted to produce a permeate product that met the Chemical Grade Propylene (CGP) specifications of 95 percent propylene. The vapor rate in the column was set so that the column bottoms product met LPG specifications.

The composition of the membrane feed has again been lowered and the rate of the vapor sidedraw increased to adjust the membrane feed enthalpy and Membrane Efficiency Index. The reflux ratio was adjusted to make overhead liquid product that met PGP specifications, and the membrane area was adjusted to produce permeate that met CGP specifications. The results of these calculations are shown in Table V. As the sidedraw propylene content was lowered, the amount of PGP produced decreased and the amount of CGP increased. Above approximately 83 percent propylene in the membrane feed, membrane cooling was sufficient to completely condense (and subcool) the nonpermeate and cooler 346 was not needed to liquefy the nonpermeate. As the membrane feed propylene content decreased below about 83 percent, nonpermeate recycle increased and membrane cooling was not sufficient to completely condense the nonpermeate, thereby requiring the use of cooler 346. This transition requiring the use of cooler 346 occurred when the Membrane Efficiency Index was approximately 1.

TABLE V

DISTILLATION COLUMN SIDEDRAW FOR A PURIFIED
PERMEATE OF 95 PERCENT PROPYLENE

| SIDEDRAW PROPYLENE, PERCENT | RATIO OF PGP PRODUCT to CGP PRODUCT | EXCHANGER DUTY† | MEI†† |
|---|---|---|---|
| 90 | 1.8 | NA | 1.03 |
| 85 | 0.46 | NA | 1.02 |
| 80 | 0.31 | 0.28 | 0.97 |

†Duty is cooler 346 duty to condense non-permeate stream, BTU/Hr × $10^{-3}$.
††MEI is Membrane Efficiency Index.

This example shows that the apparatus shown in FIG. 3 is the preferred way to simultaneously produce two desirable propylene-rich products and a desirable propane-rich product. The use of a pump to pressurize the nonpermeate was preferred since it eliminated costly gas compression. This example showed that the relative amounts of the two propylene-rich products (PGP and CGP) could be adjusted using the membrane feed propylene content, sidedraw rate, and Membrane Efficiency Index. The market demand and value of each of the propylene-rich products would guide this adjustment. Adjustment of the Membrane Efficiency Index also made it possible to eliminate the nonpermeate cooler and the capital and operating costs associated with it.

For the purposes of the present invention, "predominantly" is defined as more than about fifty percent. "Substantially" is defined as occurring with sufficient frequency or being present in such proportions as to measurably affect macroscopic properties of an associated compound or system. Where the frequency or proportion for such impact is not clear, substantially is to be regarded as about twenty per cent or more. The term "a feedstock consisting essentially of" is defined as at least 95 percent of the feedstock by volume. The term "essentially free of" is defined as absolutely except that small variations which have no more than a negligible effect on macroscopic qualities and final outcome are permitted, typically up to about one percent.

That which is claimed is:

1. A continuous process for separation of purified products from a fluid mixture by utilization of an integrated distillation and membrane separation apparatus which process comprises:
   providing a separation apparatus comprising
   (a) a fractional distillation column having an overhead vapor outlet in flow communication with a compressor, and an external heat transfer surface having one side disposed to contact fluid at the bottom of the column and the opposite side to contact compressed overhead vapor,
   (b) the compressor in fluid communication with means for proportioning compressed vapor between the heat transfer surface, a reflux condenser, and a cooler, said cooler is in flow communication with a per-selective membrane device,
   (c) the membrane device comprising a solid perm-selective membrane which under suitable differential of a driving force exhibits a permeability of at least 0.1 Barrer, channels having at least one inlet and one outlet for flow of fluid in contact with a first side of the membrane, and contiguous with the opposite side thereof a permeate chamber having at least one outlet for flow of permeate, and
   (d) Means for flow communication between the opposite side of the heat transfer surface and the fractional distillation column,
   Separating by fractional distillation a feedstock comprising a fluid mixture including a low-boiling point component and a high boiling point component, and thereby provide a vapor stream enriched in the low-boiling point component to the compressor;
   compressing the overhead vapor, and distributing portion thereof between the heat transfer surface, the reflux condenser, and the membrane device; and
   Separating from the stream distributed into the membrane device a permeate and non-permeate stream by selective permeation while controlling enthalpy of the distributed stream by controlling temperature thereof, and thereby maintain Membrane Efficiency Index of the non-permeate effluent stream within a range from about 0.5 to 1.5; and
   directing fluid from the opposite side of the heat transfer surface to the fractional distillation column.

2. The process according to claim 1 wherein at least a portion of the non-permeate fluid is returned to the fractional distillation column.

3. The process according to claim 1 wherein purified permeate stream comprises at least 95 percent propylene.

4. The process according to claim 1 wherein the feedstock comprises a mixture of an alkane compound having from 2 to about 4 carbon atoms and an alkene compound having the same number of carbon atoms as the predominate component of the feedstream.

5. The process according to claim 4 wherein the mixture has a liquid volume ratio of the alkene to the alkane compounds, and ratio is in a range of from about 1.5 to about 4.

6. An integrated distillation and membrane separation apparatus comprising:
   a fractional distillation column having an overhead vapor outlet in flow communication with a compressor, a heat transfer surface having one side disposed to contact fluid at the bottom of the column and the opposite side to contact compressed overhead vapor;
   the compressor in flow communication with means for proportioning compressed vapor between the heat transfer surface, a reflux condenser, and a cooler which is in flow communication with a perm-selective membrane device;
   the membrane device comprising a solid perm-selective membrane, which under a suitable differential of a diving force exhibits a permeability of at least 0.1 Barrer,
   channels having at least one inlet and outlet for flow of fluid in contact with a first side of the membrane, and contiguous with an opposite side thereof a permeate chamber having at least on outlet for flow of permeate; and
   means for flow communication between the opposite side of the heat transfer surface and the fractional distillation column.

7. The apparatus according to claim 6 further comprising means for flow communication between the non-permeate outlet of the membrane device and the fractional distillation column.

* * * * *